United States Patent [19]
Etoh

[11] Patent Number: 6,046,194
[45] Date of Patent: Apr. 4, 2000

[54] AGENTS FOR PREVENTING ADHESION OF AQUATIC ORGANISMS

[75] Inventor: Hideo Etoh, Shimizu, Japan

[73] Assignee: Nissan Chemical Industries, Ltd., Tokyo, Japan

[21] Appl. No.: 09/101,873

[22] PCT Filed: Jan. 28, 1997

[86] PCT No.: PCT/JP97/00180

§ 371 Date: Jul. 30, 1998

§ 102(e) Date: Jul. 30, 1998

[87] PCT Pub. No.: WO97/27751

PCT Pub. Date: Aug. 7, 1997

[30] Foreign Application Priority Data

Jan. 30, 1996 [JP] Japan .................................. 8-14244
Aug. 1, 1996 [JP] Japan ................................. 8-203449

[51] Int. Cl.⁷ .................................................. A01N 43/66
[52] U.S. Cl. .......................................................... 514/241
[58] Field of Search ............................. 544/192; 514/241

[56] References Cited

U.S. PATENT DOCUMENTS

| | | | |
|---|---|---|---|
| 4,351,834 | 9/1982 | Takahashi et al. | 424/249 |
| 4,673,513 | 6/1987 | Powell | 210/756 |
| 5,264,572 | 11/1993 | Endo et al. | 544/193 |
| 5,342,593 | 8/1994 | Christiansen et al. | 423/242.6 |

FOREIGN PATENT DOCUMENTS

| | | |
|---|---|---|
| 342 685 | 11/1989 | European Pat. Off. . |
| WO 91/18510 | 12/1991 | WIPO . |
| WO 98/07322 | 2/1998 | WIPO . |

*Primary Examiner*—S. Mark Clardy
*Assistant Examiner*—Alton Pryor
*Attorney, Agent, or Firm*—Oliff & Berridge, PLC

[57] ABSTRACT

Agents for preventing the adhesion of aquatic organisms which contain as the active ingredient isocyanuric acid compounds of formula (1)

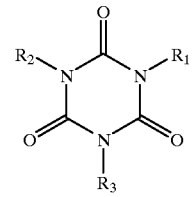

(1)

wherein $R_1$, $R_2$ and $R_3$ each independently represent a hydrogen atom or a straight chain or branched alkyl group having 1 to 8 carbon atoms. These agents are employed in the form of antifouling coatings for, e.g., ship bottoms and watercourses, solutions, or emulsions for fishing nets.

15 Claims, No Drawings

AGENTS FOR PREVENTING ADHESION OF AQUATIC ORGANISMS

This appln. is a 371 of PCT/JP97/00180 filed Jan. 28, 1997.

TECHNICAL FIELD

The present invention relates to agents for preventing the adhesion of aquatic organisms, particularly to agents for preventing the adhesion of harmful aquatic organisms such as shells to fishing nets, bottoms of ships, marine equipment such as buoys, marine constructions, circulating water systems in thermal or atomic power plants, inlet channels for heat exchanger cooling water in chemical industry, underwater constructions and reservoirs.

BACKGROUND ART

Shells and algae, such as blue mussel (*Mytilus edulis*), barnacle (Balanus sp.), oyster, Hydrozoa, hydra (Hydra sp.), serpula (Serpula sp.), ascidian, bryozoan, pond snail, sea lettuce (Ulva sp.), Enteromorpha sp., and Ectocarpus sp. are adhered and grown on portions which always contact sea water or fresh water, such as fishing nets, bottoms of ships, marine equipment such as buoys, marine constructions, thermal or atomic power plants, inlet channels for cooling water in various fields of industries, underwater constructions, such as equipment attached to a dam, and reservoirs.

If those aquatic organisms are adhered to breeding nets, openings of nets are clogged. As a result, growth of breeding fishes is inhibited with decrease of circulation of sea water, resulting in many occurrence of fish diseases.

The adhesion of those aquatic organisms to ships causes increase of fluid resistance, resulting in decrease of navigation speed, increase of fuels consumed, loss of cost for cleaning ship bottoms and cost due to suspension of the service, and the like.

In marine equipment, and marine and underwater constructions, the adhesion of aquatic organisms invites weight increase and considerable disadvantage in handling operation. The adhesion to inlet channels causes decrease of thermal conductivity, and also causes the problems that inlet channels are clogged, and the amount of water intaken is decreased.

Conventionally, in order to prevent the adhesion and propagation of marine and fresh water aquatics, antifouling coating comprising organic tin compounds such as bis(tributyltin) oxide, or copper compounds such as copper sulfate or cuprous oxide have been used Further, with respect to isocyanuric acid compounds which are the active ingredient in the present invention, use as a composition for exterminating harmful insects to woody materials (agents for exterminating termites) is disclosed in Japanese Patent Application Laid-open No. Sho 54-147924, use as a soil treating agent for ant proof is disclosed in Japanese Patent Application Laid-open No. Sho 64-3, use as ant-proof power wires is disclosed in Japanese Patent Application Laid-open No. Hei 2-78110, and use as a repellent for phlebotomic insects (repellent for mosquitoes) is disclosed in Japanese Patent Application Laid-open No. Hei 4-164003.

Though being effective in preventing the adhesion of aquatics, the above-mentioned organic tin compounds are highly toxic, and are especially prone to accumulate in the bodies of fishes and shellfishes. For the sake of promoting the environmental pollution, the use of those compounds is now under legal controls.

For example, in the United States of America, use of organic tin ship paints is inhibited to ships of 65 feet or less by the Organic Tin Antifouling Paint Regulation (1987). In the United Kingdom, use of tributyltin-containing antifouling agents to ships of 25 m or less and marine agriculture is inhibited by the Food and Environment Protection Law (1987).

Further, in Japan, tributyltin oxide is designated as a first-class specific chemical substance, and triphenyltin compounds and tributyltin compounds are specified as a second-class chemical substances, according to the Chemical Substance Examination Rule (Kashinhow) (1990). Use of those compounds are inhibited to fishing nets.

Furthermore, it is also taken a measure of inhibition of the use of tributyltin types for ship bottom coatings (Notification by the Ministry of Transportation, 1990).

The above-mentioned copper compounds are widely used as antifouling coatings for inlet channels and ship bottoms. However, since such copper compounds contain heavy metals similar to tin compounds, the use thereof is anxious for environmental pollution in future. Therefore, it cannot be said that such compounds are preferable agents for preventing the adhesion of aquatic organisms.

Further, the above-mentioned Japanese Patent Application Laid-opens No. Sho 54-147924, No. Sho 64-3, No. Hei 2-78110 and No. Hei 4-164003 do not disclose that the isocyanuric acid compounds as the active ingredient in the present invention is effective as agents for preventing the adhesion of aquatic organisms.

DISCLOSURE OF THE INVENTION

As a result of intensive investigations to solve the above-mentioned problem, the present inventors have found that isocyanuric acid compounds which are a nitrogen-containing heterocyclic compound become agents for preventing the adhesion of aquatic organisms, which have high safety, excellent ability for preventing the adhesion or propagation of aquatic organisms, in particular shells (antifouling capability), and high practicability, and have completed the present invention.

That is, the present invention relates to agents for preventing the adhesion of aquatic organisms, characterized by containing at least one isocyanuric acid compound of formula (1)

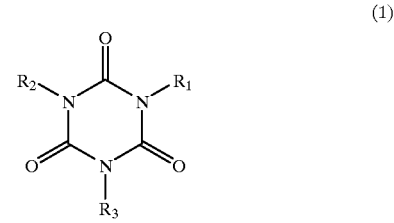

(1)

(wherein $R_1$, $R_2$ and $R_3$ each independently represent hydrogen atom or a straight or branched alkyl group having 1–8 carbon atoms).

Examples of the alkyl group having 1–8 carbon atoms for $R_1$, $R_2$ and $R_3$ in the formula are a methyl group, ethyl group, n-propyl group, iso-propyl group, n-butyl group, iso-butyl group, sec-butyl group, n-pentyl group, sec-pentyl group, iso-pentyl group, n-hexyl group, n-heptyl group, n-octyl group and 2-ethylhexyl group.

The compound of the formula (1) can be produced according to the conventional method using isocyanuric acid as a raw material in the light of methods described in Japanese Patent Publications No. Sho 35-17566, No. Sho 36-3985, No. Sho 36-4376, No. Sho 40-2556, No. Sho 40-6635, No. Sho 41-1065, No. Sho 42-9345, No. Sho. 42-12913 and so forth.

Examples of preferred combinations of $R_1$, $R_2$ and $R_3$ are described below.

$R_1$, $R_2$ and $R_3$ each independently are a straight chain or branched alkyl group having 1–8 carbon atoms;

$R_1$, $R_2$ and $R_3$ are the same straight chain or branched alkyl group having 1–8 carbon atoms to each other;

$R_1$, $R_2$ and $R_3$ each independently are a straight chain or branched alkyl group having 1–4 carbon atoms;

$R_1$, $R_2$ and $R_3$ are the same straight chain or branched alkyl group having 1–4 carbon atoms to each other;

$R_1$, $R_2$ and $R_3$ are a methyl group;

$R_1$, $R_2$ and $R_3$ are an ethyl group;

$R_1$, $R_2$ and $R_3$ are an n-propyl group; and $R_1$, $R_2$ and $R_3$ are an n-butyl group.

Examples of the alkyl group having 1–4 carbon atoms are alkyl groups having the corresponding number of carbon atoms in the exemplified alkyl group having 1–8 carbon atoms mentioned above.

The isocyanuric acid compound used as the active, ingredient in the present invention may be constituted of a single compound or a mixture of several kinds of isocyanuric acid compounds.

Further, agents for preventing the adhesion of aquatic organisms other than the isocyanuric acid compounds of the present invention can be added to the isocyanuric acid compound used as the active ingredient in the present invention for use.

The agents for preventing the adhesion of aquatic organisms of the present invention can be used by preparing it in the form of coatings, solutions, emulsions and the like.

Preparation of those coatings, solutions, emulsions and the like can employ general formulation usually practiced.

Where the agents for preventing the adhesion of aquatic organisms of the present invention are used in the form of antifouling coatings, the isocyanuric acid compound which is the active ingredient, for example, is blended with a film-forming agent to prepare a coating, and the coating is coated on bottoms of ships, marine constructions, intake pipe-lines for cooling water or underwater constructions, whereby the adhesion and propagation of aquatic organisms can be prevented.

Oil varnishes, synthetic resins, artificial rubbers and the like are used as the film-forming agent (a binder for paint).

If necessary, solvents, pigment or the like may be used.

The solvents used are xylene, toluene, cumene, methyl ethyl ketone, methyl isobutyl ketone, acetone, and the like.

In the case of preparing the paint, the isocyanuric acid compound as the active ingredient does not have the upper limitation on the concentration so long as the paint film can be formed, but the compound is blended in the proportion of 1–50% by weight, preferably 5–20% by weight, based on the weight of the antifouling coatings.

The paint film formed by coating the paint for ship bottoms may be a multilayer (or multi-stage peeling type) paint film such that the paint film has a smooth surface at the time of coating, but where the smooth surface becomes a rough surface due to the adhesion of aquatic organisms, the paint films are peeled several times by the increase of resistance of water fluid, thereby forming a fresh smooth surface. By admixture of the agents for preventing the adhesion of aquatic organisms of the present invention, the adhesion of aquatic organisms is markedly retarded, and it is an expected effect that loss speed of the paint film due to peeling is decreased.

Where the agents for preventing the adhesion of aquatic organisms of the present invention are used in the form of solutions, a solution is prepared by dissolving the isocyanuric acid compound as the active ingredient in, for example, a solvent together with a film-forming agent, and the solution is coated on fishing nets for breeding, fixed fishing nets or the like, thereby allowing the adhesion and propagation of aquatic organisms to be prevented.

Examples of the film-forming agent (binder for paint) used are synthetic resins, artificial rubbers, natural resins, and the like, and examples of the solvent used are xylene, toluene, cumene, methyl ethyl ketone, methyl isobutyl ketone, acetone and the like.

Further, if necessary, additive such as plasticizers may be added for use.

In the case of preparing the solution, the isocyanuric acid compound as the active ingredient does not have the upper limit on the concentration so long as the solution can be formed, but the compound is blended in the proportion of 1–50% by weight, and preferably 5–30% by weight, based on the weight of the solution.

Where the agents for preventing the adhesion of aquatic organisms of the present invention are used in the form of emulsions, surface active agents are added to a solution of the isocyanuric acid compound as the active ingredient according to the general method in normally preparing emulsions, thereby preparing the desired emulsions. The added type and amount of the surface active agents used can be selected according to the conventional methods.

The emulsions thus prepared can be used by mixing in raw materials, such as polymeric resins, of fishing nets for breeding, fixed fishing nets or the like used in sea or water.

In the case of preparing emulsion, the isocyanuric acid compound as the active ingredient does not have the upper limit on the concentration so long as the solution can be formed, but the compound is blended in the proportion of 1–50% by weight, preferably 3–30% by weight, based on the weight of the solution.

Further, the above-mentioned solutions or emulsions of the present invention can be used by adding to service water, reservoir water or the like in order to prevent the adhesion and propagation of aquatic organisms in intake pipe-lines of cooling water or reservoir.

BEST MODE OF CARRYING OUT THE INVENTION

The present invention will be described specifically and in detail below by referring to the examples and comparative examples, but the present invention is not limited thereto.

Formulation examples are shown in the case of using the agents for preventing the adhesion of aquatic organisms as antifouling coatings.

| Formulation Example 1 | |
| --- | --- |
| Component | % by weight |
| Isocyanuric acid tri n-propyl ester | 8 |
| VYHH (vinyl type synthetic resin, manufactured by UCC Co., Ltd.) | 7 |
| Rosin | 7 |
| Tricresyl phosphate | 3 |
| Talc | 20 |

-continued

| Component | % by weight |
|---|---|
| Barium sulfate | 15 |
| Red iron oxide | 10 |
| Xylene | 20 |
| Methyl isobutyl ketone | 10 |
| | 100 |

Formulation Example 2

| Component | % by weight |
|---|---|
| Isocyanuric acid tri n-propyl ester | 5 |
| CR-10 (chlorinated rubber resin, manufactured by Asahi Denka Kogyo K.K.) | 13 |
| Zinc flower | 20 |
| Talc | 20 |
| Plasticizer | 2 |
| Red iron oxide | 10 |
| Xylene | 30 |
| | 100 |

Formulation Example 3

| Component | % by weight |
|---|---|
| Isocyanuric acid trimethyl ester | 8 |
| VYHH (vinyl type synthetic resin, manufactured by UCC Co., Ltd.) | 7 |
| Rosin | 7 |
| Tricresyl phosphate | 3 |
| Talc | 20 |
| Barium sulfate | 15 |
| Red iron oxide | 10 |
| Xylene | 20 |
| Methyl isobutyl ketone | 10 |
| | 100 |

Formulation Example 4

| Component | % by weight |
|---|---|
| Isocyanuric acid trimethyl ester | 5 |
| CR-10 (chlorinated rubber resin, manufactured by Asahi Denka Kogyo K.K.) | 13 |
| Zinc flower | 20 |
| Talc | 20 |
| Plasticizer | 2 |
| Red iron oxide | 10 |
| Xylene | 30 |
| | 100 |

Formulation Example 5

| Component | % by weight |
|---|---|
| Isocyanuric acid tri n-butyl ester | 8 |
| VYHH (vinyl type synthetic resin, manufactured by UCC Co., Ltd.) | 7 |
| Rosin | 7 |
| Tricresyl phosphate | 3 |
| Talc | 20 |
| Barium sulfate | 15 |
| Red iron oxide | 10 |
| Xylene | 20 |
| Methyl isobutyl ketone | 10 |
| | 100 |

Formulation Example 6

| Component | % by weight |
|---|---|
| Isocyanuric acid tri n-butyl ester | 5 |
| CR-10 (chlorinated rubber resin, manufactured by Asahi Denka Kogyo K.K.) | 13 |
| Zinc flower | 20 |

-continued

| Component | % by weight |
|---|---|
| Talc | 20 |
| Plasticizer | 2 |
| Red iron oxide | 10 |
| Xylene | 30 |
| | 100 |

Formulation Example 7

| Component | % by weight |
|---|---|
| Isocyanuric acid triethyl ester | 8 |
| VYHH (vinyl type synthetic resin, manufactured by UCC Co., Ltd.) | 7 |
| Rosin | 7 |
| Tricresyl phosphate | 3 |
| Talc | 20 |
| Barium sulfate | 15 |
| Red iron oxide | 10 |
| Xylene | 20 |
| Methyl isobutyl ketone | 16 |
| | 100 |

Formulation Example 8

| Component | % by weight |
|---|---|
| Isocyanuric acid triethyl ester | 5 |
| CR-10 (chlorinated rubber resin, Manufactured by Asahi Denka Kogyo K.K.) | 13 |
| Zinc flower | 20 |
| Talc | 20 |
| Plasticizer | 2 |
| Red iron oxide | 10 |
| Xylene | 30 |
| | 100 |

Next, the formulation examples are shown in the case of using as solutions.

Formulation Example 9

| Component | % by weight |
|---|---|
| Isocyanuric acid tri n-propyl ester | 10 |
| Rosin WW | 13 |
| Toyoparax A40 (Chloroparaffin, manufactured by Tosoh Corporation) | 1 |
| Xylene | 76 |
| | 100 |

Formulation Example 10

| Component | % by weight |
|---|---|
| Isocyanuric acid tri n-butyl ester | 10 |
| Rosin WW | 13 |
| Toyoparax A40 (Chloroparaffin, manufactured by Tosoh Corporation) | 1 |
| Xylene | 76 |
| | 100 |

EXAMPLE 1

1.6 mg, 0.8 mg and 0.4 mg of isocyanuric acid tri n-propyl ester each were completely dissolved in about 1 ml of acetone, and each of the resulting sample solutions was uniformly coated on a zone having a diameter of 4 cm drawn on test paper.

A zone having only acetone coated on the test paper was provided as a blank, and zones having 1.0 mg and 0.5 mg of copper sulfate each coated thereon were provided as comparative agent.

After drying, four blue mussel (*Mytilus edulis*) having a shell length of about 2–2.5 cm were adhered to the circumference of the respective zones using a rubber piece as a spacer. The prepared test plates were dipped in a water tank into which sea water flows, and the tank was allowed to stand in a dark place for 3 hours. The test plates were taken out of the water tank, and the adhered position of byssus of blue mussel (*Mytilus edulis*) and the number thereof were counted.

In comparison with copper sulfate used as the comparative agent, the effect for preventing the adhesion (adhesion repellent activity) was obtained.

The evaluation method of the adhesion repellent activity was used according to Kazuo Ina and Hideo Etoh, "Evaluation method of adhesion repellent substances to marine adhesion organisms using blue mussel (*Mytilus edulis*)" (Kagaku to Seibutsu (Chemistry and Biology), Vol. 28 (No. 2), pages 132–138 (1990)).

The results are shown in Table 1.

EXAMPLE 2

The test was conducted in the same manner as in Example 1 except that 1.0 mg and 0.5 mg of isocyanuric acid trimethyl ester were used in place of isocyanuric acid tri n-propyl ester. The results are shown in Table 1.

EXAMPLE 3

The test was conducted in the same manner as in Example 1 except that 1.9 mg of isocyanuric acid tri n-butyl ester was used in place of isocyanuric acid tri n-propyl ester. The results are shown in Table 1.

EXAMPLE 4

The test was conducted in the same manner as in Example 1 except that 1.4 mg of isocyanuric acid triethyl ester was used in place of isocyanuric acid tri n-propyl ester. The results are shown in Table 1.

TABLE 1

| Active Ingredient | Amount of agents (mg) | Judgement |
| --- | --- | --- |
| Example 1 | | |
| Isocyanuric acid tri n-propyl ester | 1.6 | ++ |
| | 0.8 | ++ |
| | 0.4 | ++ |
| Example 2 | | |
| Isocyanuric acid trimethyl ester | 1.0 | ++ |
| | 0.5 | ++ |
| Example 3 | | |
| Isocyanuric acid tri n-butyl ester | 1.9 | ++ |
| Example 4 | | |
| Isocyanuric acid triethyl ester | 1.4 | ++ |

TABLE 1-continued

| Active Ingredient | Amount of agents (mg) | Judgement |
| --- | --- | --- |
| Comparative Agent | | |
| Copper sulfate | 1.0 | ++ |
| | 0.5 | + |
| Blank | – | – |

It is noted that symbols in the Table have the following means:

++: No adhesion at all in the zone, and strong repellent effect is observed.

+: Adhesion in the zone is observed, but adhesion is substantially outside the zone, and repellent effect is observed.

–: Adhesion is observed inside and outside the zone to the same extent, and repellent effect is not observed.

EXAMPLE 5

Butyral resin (Eslex BL-2, manufactured by Sekisui Chemical Co., Ltd.) was prepared in 15% W/W using a mixed solvent of toluene:methanol=1:1.

10 mg of isocyanuric acid tri n-propyl ester was placed in Disposable Culture Tube ($\phi$ 12 mm×75 mm, manufactured by Iwaki Glass Co.), and dissolved in 1 ml (about 700 mg) of the above-mentioned resin solution. The resulting solution was coated on a sample zone having a diameter of 5 cm drawn on a test plate (polyvinyl chloride plate, 350×600 mm).

A sample zone on which only the above-mentioned resin solution was coated was provided as a blank.

After drying, the test plate was dipped in sea at a depth of about 1 m at Motimune fishing port of Shizuoka-city. The test plate was periodically taken out of the sea, and the adhesion state of organisms was visually observed.

The presence or absence of antifouling activity was represented by day when the adhesion is prevented by comparing the adhesion state of organisms in the sample zone with the blank. As a result, isocyanuric acid tri n-propyl ester showed good antifouling activity for about 60 days.

Incidentally, this test was conducted from the beginning of May in which activity (adhesion) of organisms was vigorous.

EXAMPLE 6

Butyral resin (Eslex BL-2, manufactured by Sekisui Chemical Co., Ltd.) was prepared in 15% W/W using a mixed solvent of toluene:methanol=1:1.

12 mg of isocyanuric acid tri n-butyl ester was placed in Disposable Culture Tube ($\phi$ 12 mm×75 mm, manufactured by Iwaki Glass Co.), and dissolved in 1 ml (about 700 mg) of the above-mentioned resin solution. The resulting solution was coated on a sample zone having a diameter of 5 cm drawn on a test plate (polyvinyl chloride plate, 350×600 mm).

A sample zone on which only the above-mentioned resin solution was coated was provided as a blank.

After drying, the test plate was dipped in sea at a depth of about 1 m at Motimune fishing port of Shizuoka-city. The test plate was periodically taken out of the sea, and the adhesion state of organisms was visually observed.

The presence or absence of antifouling activity was represented by day when the adhesion is prevented by comparing the adhesion state of organisms in the sample zone with the blank. As a result, isocyanuric acid tri n-butyl ester showed good antifouling activity for about 90 days.

Incidentally, this test was conducted from the beginning of July in which activity (adhesion) of organisms was vigorous.

POSSIBILITY OF INDUSTRIAL APPLICATION

The agents for preventing the adhesion of aquatic organisms containing isocyanuric acid compounds of the formula (1) as the active ingredient has high safety, and also excellent organism adhesion preventing capability (antifouling capability) by which the adhesion or propagation of aquatic organisms, particularly shells, is prevented.

What is claimed is:

1. A method that prevents the adhesion of aquatic organisms, comprising contacting to an aquatic system containing aquatic organisms an agent characterized by containing at least one kind of isocyanuric acid compounds of formula (1)

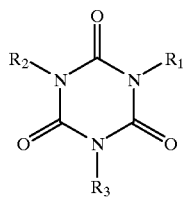

(1)

(wherein $R_1$, $R_2$ and $R_3$ each independently represent hydrogen atom or a straight chain or branched alkyl group having 1–8 carbon atoms).

2. The method that prevents the adhesion of aquatic organisms as claimed in claim 1, wherein $R_1$, $R_2$ and $R_3$ each independently represent a straight chain or branched alkyl group having 1–8 carbon atoms.

3. The method that prevents the adhesion of aquatic organisms as claimed in claim 1, wherein $R_1$, $R_2$ and $R_3$ are the same to each other.

4. The method that prevents the adhesion of aquatic organisms as claimed in claim 2, wherein $R_1$, $R_2$ and $R_3$ are a straight chain or branched alkyl group having 1–4 carbon atoms.

5. The method that prevents the adhesion of aquatic organisms as claimed in claim 2, wherein $R_1$, $R_2$ and $R_3$ are a methyl group.

6. The method that prevents the adhesion of aquatic organisms as claimed in claim 2, wherein $R_1$, $R_2$ and $R_3$ are an ethyl group.

7. The method that prevents the adhesion of aquatic, organisms as claimed in claim 2, wherein $R_1$, $R_2$ and $R_3$ are an n-propyl group.

8. The method that prevents the adhesion of aquatic organisms as claimed in claim 2, wherein $R_1$, $R_2$ and $R_3$ are an n-butyl group.

9. The method of claim 1 wherein said agent is contained in paints, solutions or emulsions.

10. The method of claim 2 wherein said agent is contained in paints, solutions or emulsions.

11. The method of claim 10 wherein said agent is contained in paints.

12. The method of claim 11 wherein said paints are paints for ship bottoms.

13. The method of claim 10 wherein said agent is contained in paints, solutions or emulsions, which are antifouling agents.

14. The method of claim 12 wherein said paints for ship bottoms are multilayer (or multi-stage peeling type) paints for ship bottoms.

15. The method of claim 11 wherein said paints are paints for inlet channels.

* * * * *